United States Patent [19]
Dykes

[11] Patent Number: 5,497,662
[45] Date of Patent: Mar. 12, 1996

[54] METHOD AND APPARATUS FOR MEASURING AND CONTROLLING REFRACTED ANGLE OF ULTRASONIC WAVES

[75] Inventor: Edward R. Dykes, San Jose, Calif.

[73] Assignee: General Electric Company, San Jose, Calif.

[21] Appl. No.: 117,851

[22] Filed: Sep. 7, 1993

[51] Int. Cl.$^6$ .................................................. G01N 29/04
[52] U.S. Cl. ........................... 73/634; 73/621; 73/598
[58] Field of Search ........................... 73/598, 621, 634, 73/633, 632, 629, 627, 620, 618

[56] References Cited

U.S. PATENT DOCUMENTS

| | | | |
|---|---|---|---|
| 3,913,386 | 10/1975 | Saglio | 73/67.5 R |
| 3,938,372 | 2/1976 | Sproule | 73/67.8 S |
| 3,969,926 | 7/1976 | Walker et al. | 73/634 |
| 3,978,714 | 9/1976 | Shraiber et al. | 73/634 |
| 4,235,112 | 11/1980 | Kaiser | 73/634 |
| 4,398,425 | 8/1983 | Matzuk | 73/634 |
| 4,475,394 | 10/1984 | Takeda et al. | 73/598 |
| 4,571,999 | 2/1986 | Arita et al. | 73/598 |
| 4,893,511 | 1/1990 | Voigt et al. | 73/634 |
| 5,125,272 | 6/1992 | Latimer et al. | 73/598 |
| 5,237,874 | 8/1993 | Latimer et al. | 73/634 |
| 5,301,552 | 4/1994 | Nagura et al. | 73/634 |

FOREIGN PATENT DOCUMENTS

3203827A1  8/1993  Germany.

*Primary Examiner*—Richard Chilcot
*Assistant Examiner*—Eric S. McCall
*Attorney, Agent, or Firm*—James E. McGinness

[57] ABSTRACT

A method and an apparatus for measuring and then controlling the refracted angle of ultrasonic waves propagating through a component. The method directly measures the actual refracted angle of ultrasound in an industrial component while performing nondestructive examination by measuring the slopes of characteristic echo-dynamic lines. These slopes are related to the angle of refraction by a simple mathematical relationship. A pattern recognition filtering method is used to identify the echo-dynamic pattern. The slope of an echo-dynamic line is computed after an edge detection algorithm is applied to the data.

11 Claims, 4 Drawing Sheets

METHOD AND APPARATUS FOR MEASURING AND CONTROLLING REFRACTED ANGLE OF ULTRASONIC WAVES

FIELD OF THE INVENTION

This invention relates generally to non-destructive examination (NDE) of material, such as metal or alloy, for voids, flaws, cracks and other defects that can be detrimental to the integrity of the material. Specifically, the invention relates to the inspection of parts and components using refracted ultrasonic waves.

BACKGROUND OF THE INVENTION

Ultrasonic examinations are performed within the nuclear industry and most other major industries to determine the condition of parts and components. The metal or alloy material of a part or component is inspected using ultrasound to detect any flaws which could prove detrimental to the safe operation of that part or component. The ultrasonic NDE method can be used to detect internal flaws in most engineering metals and alloys. Bonds produced by welding, brazing, soldering and adhesive bonding can also be ultrasonically inspected.

Ultrasonic inspection is used for quality control and materials inspection in the fabrication of structures, reactor pressure vessels, airframes, pipe systems, bridges, motor vehicles and jet engines. The present invention has application in all of these fields.

For successful application of ultrasonic examination techniques, the ultrasonic system, including transducers, must be suitable for the type of inspection being performed. If the proper transducer is not used, there is a high potential for gross error in the inspection results, or there could be no results at all. For instance, using a common ultrasonic transducer that has a hard flat-surfaced Lucite wedge for examining as-welded overlaid pipe welds results in gross errors in the ultrasonic inspection results. In many cases ultrasonic inspection data is not recorded at all. This is due to the presence of air gaps between the transducer head and the rough surface being inspected, which forms an opaque barrier.

Ultrasonic characterization of cracks in materials is at least a two-step process: 1) detection and location; and 2) sizing in absolute or relative terms. In accordance with the first step of this process, the transducer is excited to emit an ultrasonic wave which is coupled to the structure being inspected. The emitted wave enters the structure, where it is reflected by the crack. The return path of the reflected wave impinges on the transducer, where it is detected as a "pulse echo" signal.

The determination of the crack size, or depth of penetration in the case of surface-connected flaws, is a different and more complicated task. A conventional method for determining the depth of penetration of a planar crack is the back-scattered time-of-flight technique. This method takes advantage of the backward scattering of waves of ultrasonic energy at the edges of a crack. An emitter of short pulses of ultrasound, coupled to the inspection surface, causes refracted sound waves to impinge on the crack edge, which scatters the ultrasonic energy in all directions. A detector situated on the same or opposite surface as the crack is excited by scattered pulsed energy after a time delay. The time delay is a function of the crack height, the angle of refraction and other dimensions. By measuring the time-of-flight for the round trip from the transducer to the crack edge and back to the transducer, the crack height can be easily computed from the geometry.

Such ultrasonic inspections of the structural integrity of industrial components made of steel and other metals depend upon knowing the beam profiles of the ultrasonic waves that propagate into these components. It is common practice to control the refracted angle of the ultrasound by using hard shoes that follow the surface and maintain, more or less, a constant angle. Surfaces that are rough, with both short-term and long-term roughness, pose a problem because it is difficult to maintain contact. In addition, anisotropic materials, such as stainless steel weld metal and cast stainless steel components, redirect the ultrasound inside the material in an unpredictable manner.

Rough surface conditions and anisotropic grain structure can result in unpredictable results using conventional examination methods. Using the prior art, refracted angles are measured on a special calibration block, and then it is assumed that the angle is the same when applied to a specimen. Immersion inspection methods, which include tanks, booted search units, bubblers, and squirters, do not typically have a mechanism for maintaining a constant refracted angle.

The angle of refraction within a given material is controlled by the ultrasonic transducer's angle of incidence, i.e., the number of degrees by which the path of propagation is tilted relative to an axis normal to the object surface. The angle of incidence is determined in accordance with Snell's Law, which can be expressed mathematically as:

$$\sin a/\sin b = V_1/V_2$$

where a is the angle of incidence; b is the angle of refraction; $V_1$ and $V_2$ are the respective wave velocities in the first and second media. Snell's Law describes wave behavior at an interface between two different media. The law applies even if mode conversion takes place.

FIG. 1 depicts a transducer 2 as it interrogates butt-welded stainless steel piping 8 and 8'. The refracted angle θ of the beam 4 impinging upon a defect 6 in the wall of pipe 8 is uncertain due to scattering at the rough surface 10 of weld overlay 14 and the interaction with the anisotropic columnar grain structure of the weld metal of butt weld 12 and weld overlay 14. The dashed line represents the weld fusion line. The angle of incidence is denoted by α. Numeral 16 denotes a counterbore or other geometrical reflector. Variation in the entry surface and the dendritic structure of the weld metal causes variations in the angle of the ultrasonic wavefront that impinges upon the crack, or other target, within the pipe wall. A couplant 18, such as water or oil, couples the ultrasound from transducer 2 to entry surface 10. The transducer may be a conventional flat-focused probe or a phased-array unit. In the event that a phased-array electromagnetic acoustical transducer is used, a couplant is not required.

Even perfect knowledge of the surface contour does not guarantee good results when inspecting with ultrasonic beams angled from the perpendicular. Wave interactions with the internal structure of metallic components can change the direction of propagation. For example, stainless steels with coarse columnar grain structures, commonly found in casting and weld metals, can redirect ultrasonic waves and result in misleading data. In some cases, the ultrasound is redirected to the opposite surface, resulting in a strong specular reflection and an apparent target that erroneously appears to be a mid-wall defect. Another common problem is confusion between reflections arising from longitudinal waves and those arising due to shear waves.

Booted search units or immersion methods are used if the surface is too irregular for contact methods. Immersion methods are used if components can be removed and placed in a water bath. Regardless of the means of dealing with surface conditions and anisotropic materials, a measurement of the exact refracted angle of the ultrasound is a necessary parameter for accurate sizing during pulse-echo examinations, and to verify coverage of the part.

SUMMARY OF THE INVENTION

The present invention is a method and an apparatus for measuring and then controlling the refracted angle of ultrasonic waves propagating through a component. This invention provides a method for directly measuring the actual refracted angle of ultrasound in an industrial component while performing NDE, i.e., by measuring the slopes of characteristic echo-dynamic lines. These slopes are related to the angle of refraction by a simple mathematical relationship.

As previously discussed, it can be difficult to maintain a constant or nearly constant refracted angle of ultrasound with a changing surface due to the shape of the specimen, a rough surface condition, anisotropic material, etc. In addition, standard immersion methods or techniques using booted search units do not follow the surface contour, which means that the ultrasonic beam can wander in the absence of a feedback mechanism to control the refracted angle.

The ultrasonic scanning mechanism must move across a target and acquire data. In accordance with the present invention, a pattern recognition filtering method is used to identify the echo-dynamic pattern. The slope of an echo-dynamic line is computed after an edge detection algorithm is applied to the data. If two or more echo-dynamic lines of sufficient amplitude are available from the same target, then these lines may be measured and averaged, if desired.

An ultrasonic examiner can verify the refracted angle by directly observing the ultrasonic beam profile as it passes over a flaw, geometrical feature, or other reflector, using the echo-dynamic line method. This method allows the operator to accurately measure the refracted angle in order to improve the accuracy of sizing flaws and geometrical features. The echo-dynamic line method allows the operator to either measure and record the actual refracted angle for later reference and analysis of the data, or use the information to adjust the refracted angle during the examination.

Immersion inspection methods do not typically have a mechanism for maintaining a constant refracted angle. Using the echo-dynamic measurement method of the invention, the angle of refraction can be easily measured and easily adjusted without performing complex calibrations on calibration standards and without using surface profiling equipment. A simple calibration block or geometrical reflector in the specimen will allow an accurate measurement and feedback for adjustment purposes in order to maintain a constant refracted angle.

DETAILED DESCRIPTION OF THE PREFERRED EMBODIMENTS

Most reflectors in an industrial component display the same predictable relationship between motion of the transducer and the distance to the target. The ultrasonic distance to the target is commonly called the "metal-path distance." Metal path is usually displayed in inches or mm, but the physical parameter actually measured to determine metal path is the transit time. For pulse-echo examinations and dual-element type probes, transit time and metal path are related by:

$$m_p = 0.5(t - t_w)c$$

where, t is the round-trip transit time; $t_w$ is the wedge or boot delay; and c is the velocity of sound in the material.

A segment of a hyperbolic curve (an arc) is formed as the ultrasonic beam of a moving transducer passes over a reflector inside a metallic component. This arc is due to the beam spread of the transducer: one end of the arc corresponds to the leading ray of the beam and the other end of the arc corresponds to the trailing ray of the beam. The major axis of the hyperbola is perpendicular to the surface upon which the transducer moves.

Figure 1:
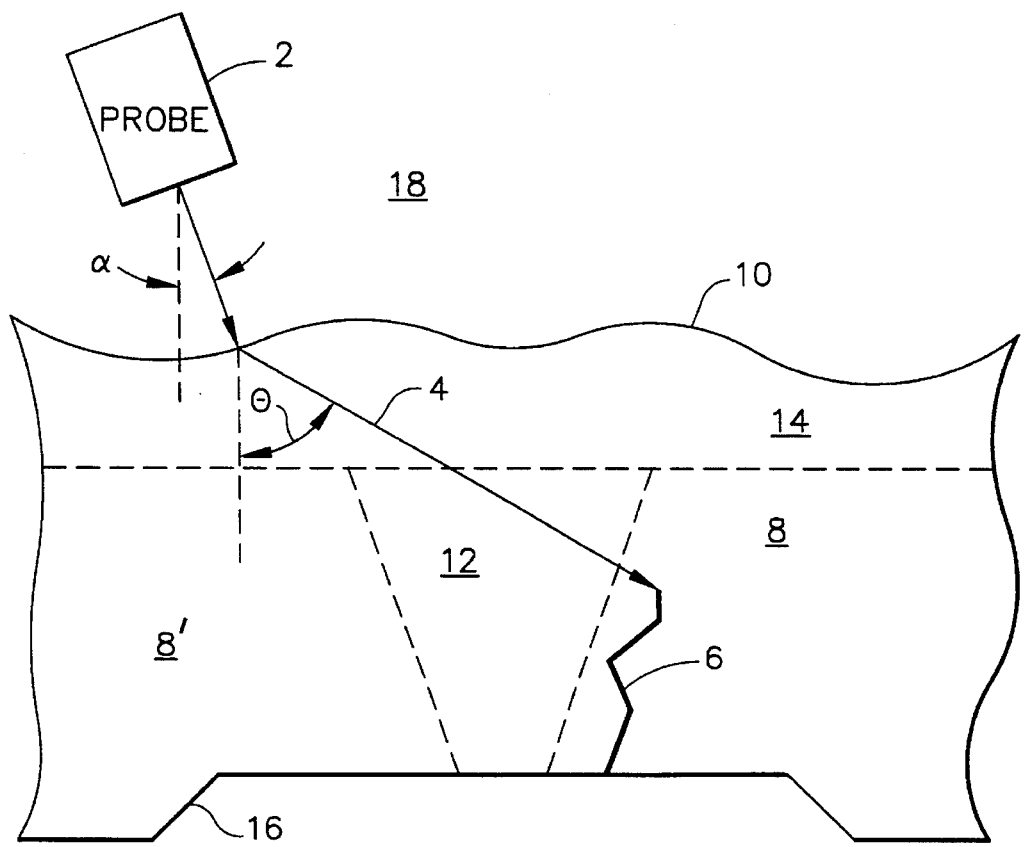
FIG. 1 is a schematic depiction of an example of an ultrasonic inspection of stainless steel piping with a rough entry surface and a transit path through weld metal.
Figure 2:
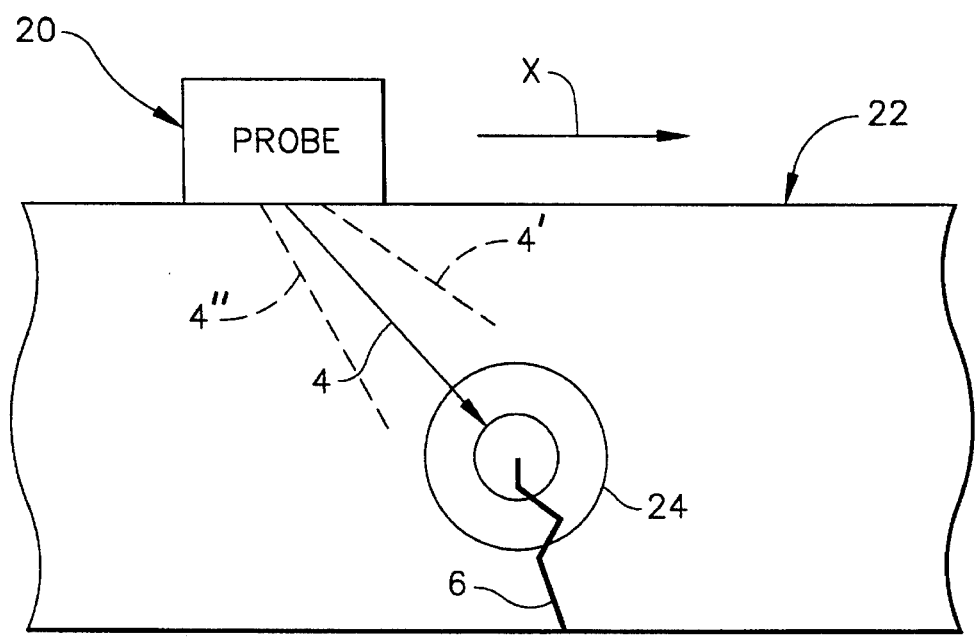
FIG. 2 is a schematic depiction of an example of an application for determining the refracted angle of ultrasound in a material using the slope of the echo-dynamic lines.

FIG. 2 shows an example of how the data is collected in order to observe the echo-dynamic lines. An automated data acquisition system may be used, or the data may be gathered manually using a standard flaw detector and a hand-held transducer. The ultrasonic probe 20 is moved over the surface of a metallic component 22 in a direction X such that the ultrasonic beam 4 sweeps across a target. Numerals 4' and 4" in FIG. 2 respectively denote the leading and trailing rays. In this instance, the target is the tip of crack 6. As the ultrasonic beam moves across a crack tip, a diffraction signal 24 caused by the discontinuity in the material is detected by probe 20. Other suitable targets include the bases of cracks, inclusions, slag, notches, holes, grain boundaries in the material, corners, edges, counterbores in pipes and all other point or line type targets.

For manual examinations, the examiner must carefully evaluate the data using an oscilloscopic trace of the signal detected by the transducer, commonly referred to as the A-scan. Using different reflections from the same feature, the operator must carefully measure the differences in metal path and transducer location in order to accurately calculate the refracted angle.

Figure 3:
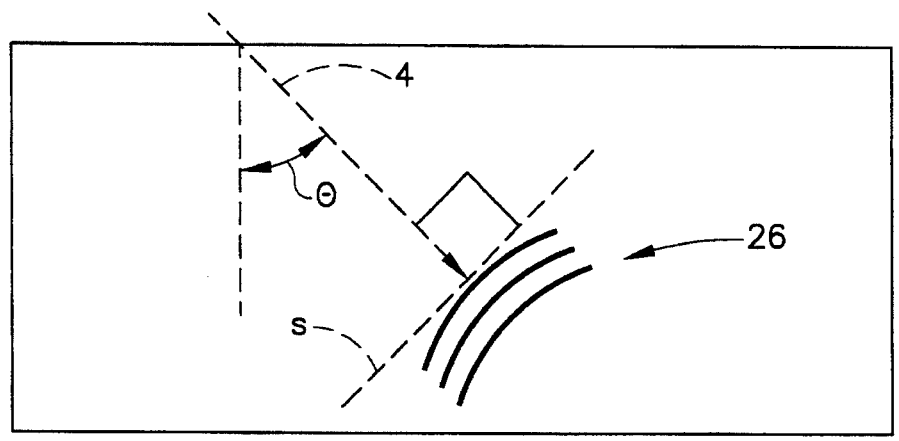
FIG. 3 is a schematic depiction of a B-scan display of the ultrasonic signals from the crack tip in FIG. 2.

FIG. 3 is a schematic depiction of the B-scan image produced by several commercially available ultrasonic imaging systems. The width of the ultrasonic beam determines the lengths of the lines (hereinafter "echo-dynamic lines") connecting the end points of the echo-dynamic arcs 26. The number of echo-dynamic arcs for a given target depends upon the characteristics of the transducer. A highly damped transducer will yield few echo-dynamic arcs (i.e., two or three), whereas a lightly damped transducer will yield many (i.e., five or more).

FIG. 3 shows that a relationship exists between the slope s of the tangent to the echo-dynamic arc at the central beam and the refracted angle θ of the ultrasonic waves. FIG. 3 simulates the image expected on an ultrasonic imaging system that maintains a physically correct 1-to-1 relationship in all dimensions. By measuring the slope s and the lengths of the echo-dynamic lines connecting the endpoints of the echo-dynamic arcs on this image, the refracted angle θ and the beam spread of the transducer can be determined. The refracted angle at which the ultrasound is propagating in the component may be determined either manually or automatically using the method of the invention.

Determining the refracted angle of ultrasound in a material is very important for ensuring appropriate coverage for detection purposes and for calculating accurate through-wall sizes. The slope of the echo-dynamic line is easily determined from a B-scan image. The B-scan can be either "corrected" or "uncorrected" for geometry. Performed manually, the operator selects two points at the extremes of an echo-dynamic arc (formed from one half-cycle of the ultrasonic pulse). If θ is the refracted angle and s is the slope of the echo-dynamic line connecting the endpoints of the corresponding echo-dynamic arc, then:

$$\theta = \arcsin [s]$$

$$s = \Delta m_p / \Delta y$$

where $\Delta m_p$ is the difference in metal path distance between two end points on an echo-dynamic arc; and $\Delta y$ is the difference in the scan axis position of the scanner corresponding to the same two points on the same echo-dynamic arc. If transit time is used, then $m_p = 0.5tc$.

The relationship between θ and s holds for either longitudinal or shear waves. Some echo-dynamic arcs may arise due to mode-converted phenomena, in which case this relationship will not hold. For example, longitudinal-wave search units have a trailing shear-wave component, and with the velocity set for longitudinal waves, shear-wave echo-dynamic lines will have a different relationship. This relationship is calculated below. Alternatively, the velocity for shear waves may be entered, and shear-wave components can be analyzed using the above formula.

The procedure for determining the refracted angle from a B-scan display entails the following steps:

(1) Enter the correct ultrasonic velocity into the ultrasonic imaging system. An error in the velocity will make the calculations of the refracted angle incorrect. If both longitudinal-wave and shear-wave indications are in the image, it is best to enter the longitudinal-wave velocity. [Note: If the longitudinal-wave velocity is used, the following calculation will be incorrect for the shear-wave indications.]

(2) Bring up the B-scan image to the area of interest. Select a target. Note its echo-dynamic arcs.

(3) Using the cursor, go to the upper edge of one feature of an echo-dynamic arc and note the metal path distance ($m_{p1}$) and the scanner location ($y_1$).

(4) Using the cursor, go to the lower edge of the echo-dynamic arc and note the metal path distance ($m_{p2}$) and the scanner location ($y_2$).

(5) Calculate the difference in the metal path distances:

$$\Delta m_p = m_{p1} - m_{p2}$$

(6) Calculate the difference in the scanner locations:

$$\Delta y = y_1 - y_2$$

(7) Calculate the slope:

$$s = \Delta m_p / \Delta y$$

"s" is a good estimate of the slope of the tangent. The refracted angle of the ultrasound detecting this target is then given by:

$$\theta = \arcsin [s]$$

The validity of the foregoing procedure can be demonstrated as follows. Assume that a flaw is d inches below the inspection surface. The distance from the y-axis location of the flaw to the y-axis location of the scanner is y. Therefore:

$$m_p^2 = y^2 + d^2$$

Differentiating with respect to y, we have:

$$2m_p [d/dy\ (m_p)] = 2y$$

From this equation, it can be derived that:

$$d/dy(m_p) = y/m_p$$

Since $y = d\tan(\theta)$ and $m_p = d/\cos(\theta)$, it follows that:

$$d/dy(m_p) = \cos(\theta)\tan(\theta) = \sin(\theta)$$

Thus:

$$\theta = \arcsin [d/dy(m_p)] = \arcsin [s]$$

From the foregoing, the slopes for a few common angles should be noted:

Slope of Echo-Dynamic Line: 0  0.5  0.707  0.866  1.0
Refracted Angle (deg): 0  30  45  60  90

In the event that shear-wave echo-dynamic lines are analyzed when using the longitudinal-wave velocity, the actual distances are only one half of the measured distances (because all reflections are assumed to be due to longitudinal waves if the longitudinal-wave velocity is used). Consequently, the actual metal path is $m_p/2$, and:

$$d/dy(m_p) = 4\sin(\theta)$$

$$\theta = \arcsin [s/4]$$

In other words, for shear waves on a longitudinal-wave display, the slope must be divided by a factor of 4 before taking the arc sine. Of course, if shear waves are analyzed with the shear-wave velocity entered, then the standard formula, $\theta = \arcsin [s]$, applies.

In the event that the imaging system used does not automatically convert time measurements to metal path distances, then this part of the calculation must be performed by the operator. If round-trip transit time is used, then $m_p = 0.5tc$, where c is the speed of ultrasound in the medium.

From an accurate measurement of the refracted angle, accurate measurements of the distance from the inspection surface to the target can be made, within the limitations of the wavelength, the instrumentation and the precision of the mechanical scanning mechanism. The distance from the inspection surface to the target is then computed from the standard formula:

$$d = m_p [\cos(\theta)]$$

The above method of computing the actual refracted angle of the ultrasound interacting with a target may be automated in order to work in a feedback control system to automatically adjust the refracted angle when using an immersion or booted ultrasonic method. Immersion methods include techniques using devices such as squirters and bubblers in addition to standard tanks filled with water or other liquids.

Figure 4:
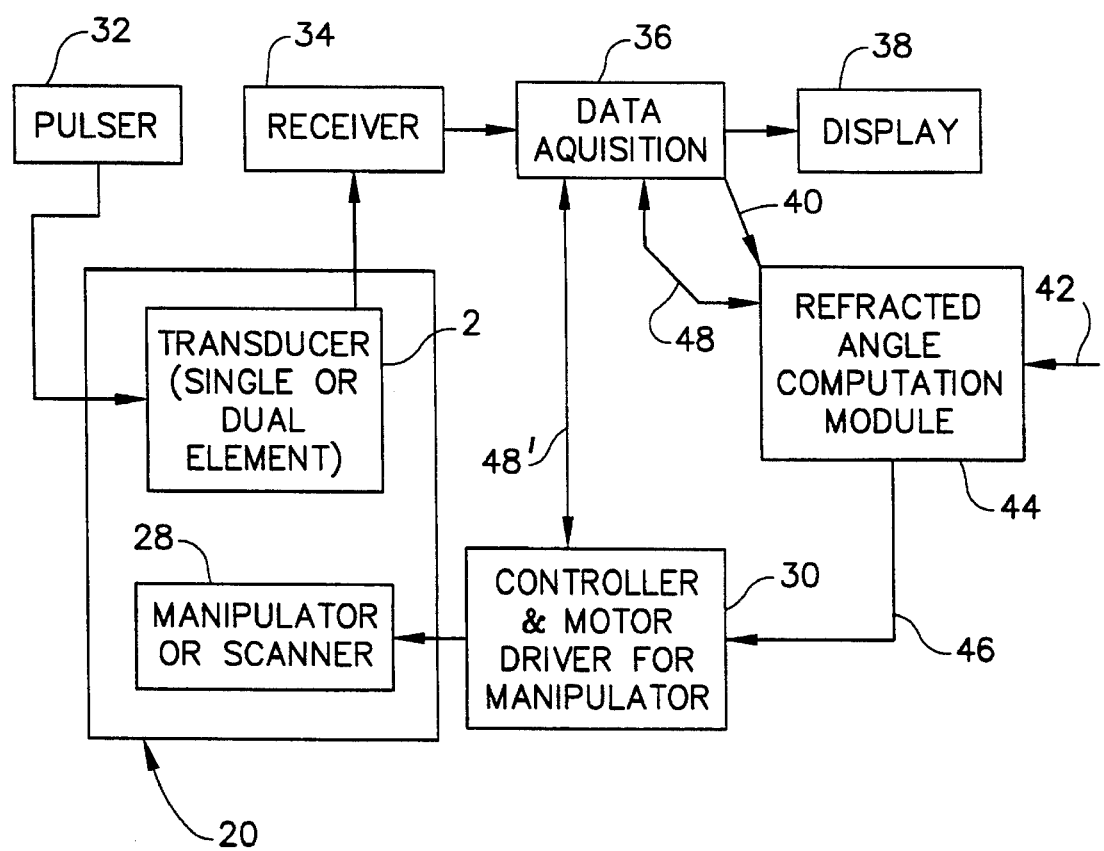
FIG. 4 is a block diagram showing the system for automatic control of the refracted angle in accordance with the invention.

FIG. 4 is a block diagram showing the system for automatic control of the refracted angle in accordance with the invention. The probe 20 comprises a single or dual-element transducer 2 and a manipulator or scanner 28 on which the transducer is mounted. The manipulator or scanner 28 varies the angle of incidence of the beam transmitted by the transducer as well as scanning the transducer in the X-Y plane. The conventional transducer is driven to transmit ultrasonic pulses by a pulser circuit 32. The return signal detected by the same transducer or another transducer located in close proximity is received by receiver circuit 34. The respective times of transmission and reception determine the transit time, which in turn is used to calculate the metal path.

In the case of a conventional transducer, the variation in the angle of incidence is controlled by a controller and motor driver subsystem 30 which causes the manipulator to physically rotate the transducer. In the case of a phased array transducer, the angle of incidence is varied via electronic rephasing. In both cases, change in the angle of incidence produces a change in the angle of refraction. The transducer has a conventional position encoder (not shown) for measuring the angular position of the transducer.

As a metallic specimen, for example, is scanned by the transducer, data is acquired by a data acquisition subsystem 36 and displayed on display 38. Subsystem 36 may comprise conventional sample-and-hold and analog-to-digital conversion circuits. Data acquisition subsystem 36 also incorporates means for controlling driver subsystem 30 and means for processing feedback signals representing scanner position from subsystem 30. Subsystem 36 outputs digitized radiofrequency waveform data with scanner positions on line 40 to a refracted angle computation module 44, which may be either hardware or a software module running on a computer with appropriate supporting input/output equipment.

Figure 5A:
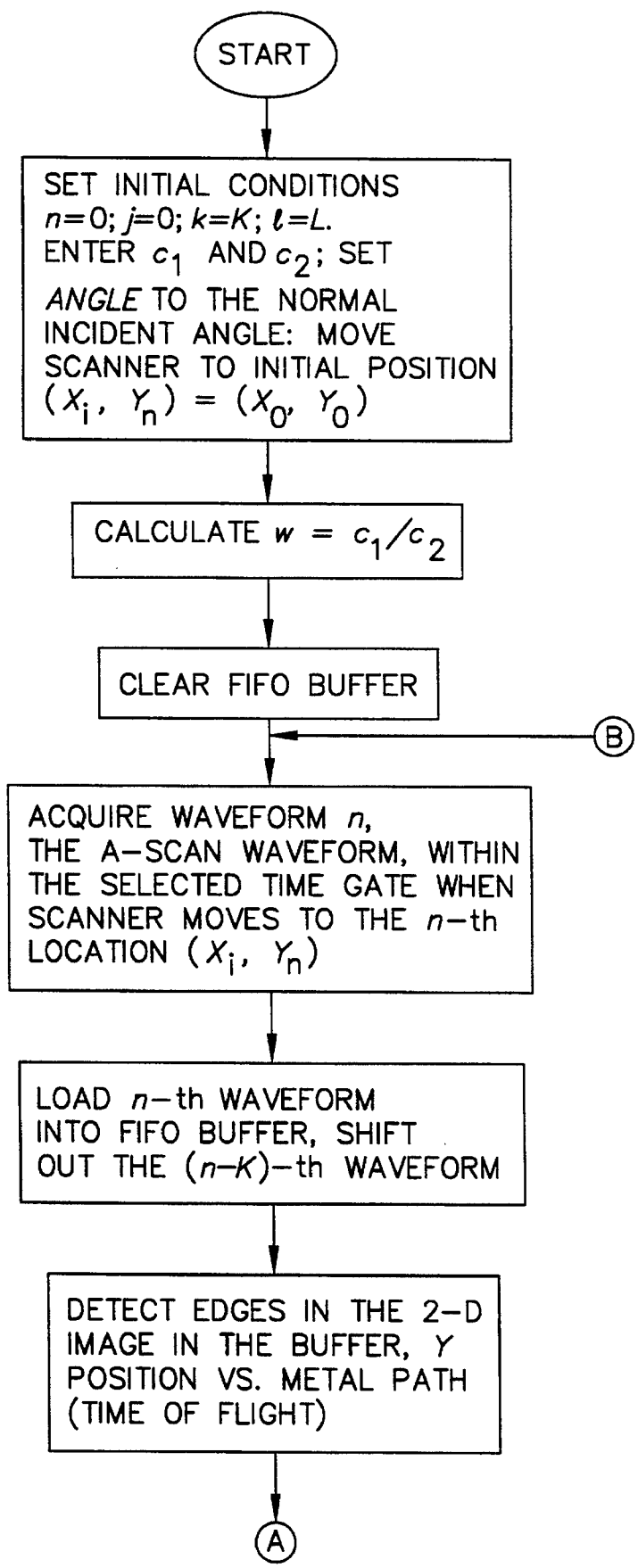
FIGS. 5A and 5B in combination show a flowchart of the method in accordance with the invention.
Figure 5B:
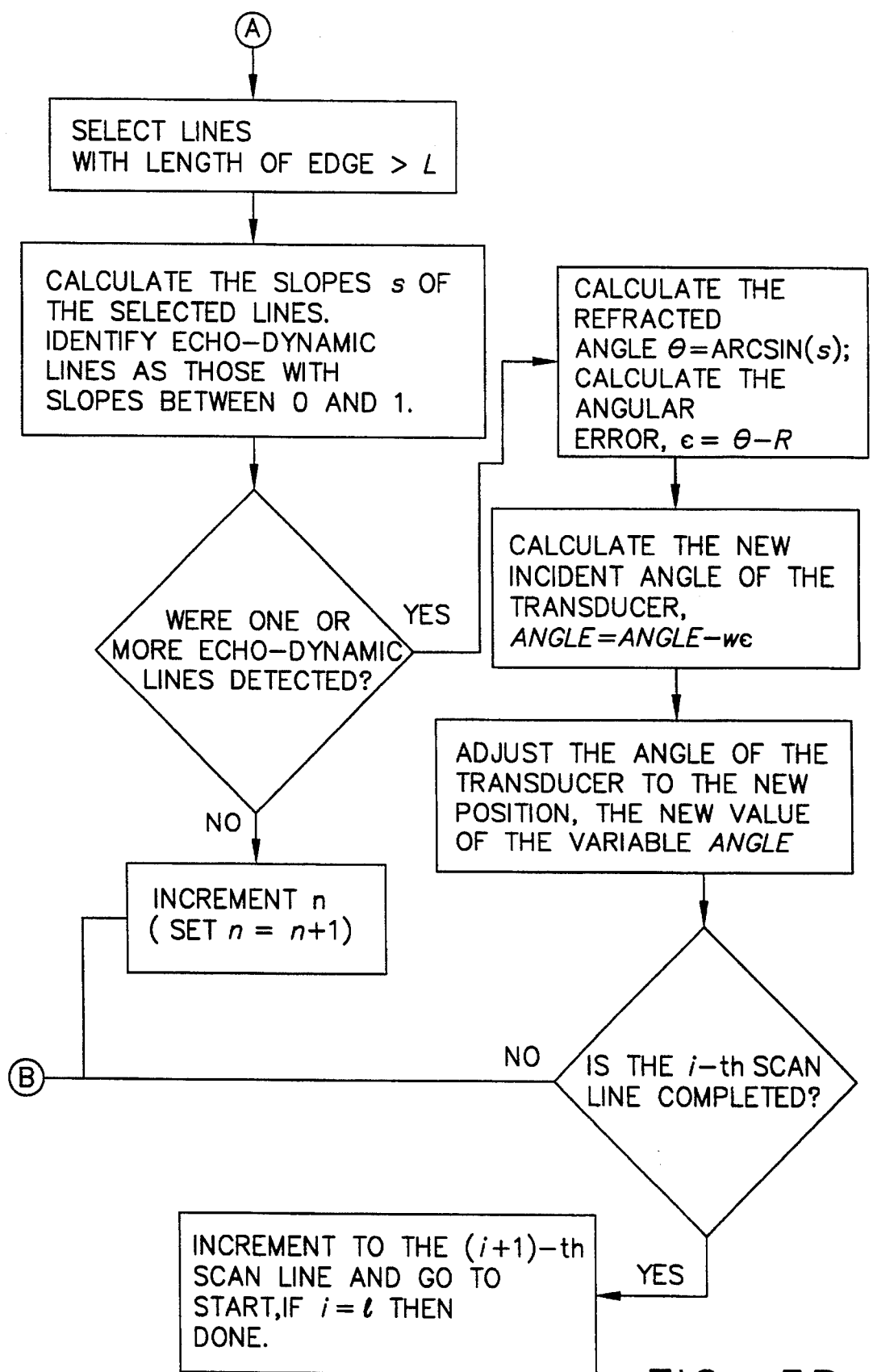

Module 44 computes the refracted angle of the main lobe of the ultrasonic wave propagating inside the specimen, based on the acquired data from subsystem 36 and compares it to a refracted angle setpoint input 42, in accordance with the algorithm shown in FIGS. 5A and 5B. First, a pattern recognition filtering method is used to identify the echo-dynamic pattern. Then the slope of an echo-dynamic line is computed after an edge detection algorithm is applied to the data. If two or more echo-dynamic arcs of sufficient amplitude are available from the same target, then the slopes for the echo-dynamic lines may be computed and averaged. Control signals and synchronizing signals for coordinating the data acquisition process are shown as line 48.

The specimen may contain calibration reflectors, or a calibration block may be scanned at the same time as the specimen is scanned, in order to obtain the necessary echo-dynamic lines for adjusting the incident angle, if necessary.

As the data collected from a particular region is analyzed, the slope of the echo-dynamic line is determined, the refracted angle is calculated and a control signal 46 is sent to the controller 30 to adjust the angle of incidence of the transmitted ultrasonic wave. This control signal could be analog or digital, depending upon the specific implementation selected.

The echo signal must be properly time-gated in order that extraneous signals not give rise to erroneous results. The algorithm is shown in detail in FIGS. 5A and 5B. The initial conditions include: n, the number of y axis increments; i, the number of x axis increments; k, the number of waveforms held in the FIFO buffer; ANGLE, the angle of incidence setting provided by a position encoder on the transducer which measures the angle of incidence; $c_1$, the velocity of sound in water or other material used to couple the sound into the specimen; $c_2$, the velocity of sound in the specimen. R is the desired angle of refraction.

An edge detection algorithm operates on the FIFO buffer in order to detect those arcs which may be echo-dynamic arcs. It is best to use radiofrequency data, i.e., the bipolar waveform, because it is important to select lines representing only one feature. For example, an echo-dynamic line formed by a positive-going half-wave is a feature distinct from one formed by a negative-going half-wave. The criteria used to select echo-dynamic arcs is based upon the observations that the echo-dynamic arcs must have an endpoint-to-endpoint distance which is comparable to the beam width of the transducer and that the echo-dynamic lines connecting those endpoints must have a slope between zero and unity. The minimum length of the echo-dynamic lines that is acceptable is a user-selectable parameter L.

The foregoing method and apparatus have been disclosed for the purpose of illustration. Variations and modifications of the disclosed apparatus will be readily apparent to practitioners skilled in the art of ultrasonic detection. All such variations and modifications are intended to be encompassed by the claims set forth hereinafter.

I claim:

1. A method for measuring an angle of refraction of a pulsed ultrasonic beam propagating through a solid material after said beam has been transmitted by an ultrasonic transducer to impinge on a surface of said solid material with a predetermined angle of incidence, comprising the steps of:

moving said transducer from a first position to a second position;

transmitting a pulsed ultrasonic beam and then receiving an echo pulse from a reflector at each of a plurality of transducer positions along a path from said first position to said second position;

organizing data for the positions of said transducer and data for metal paths corresponding to said position data to represent an echo-dynamic arc;

recognizing said echo-dynamic arc using pattern recognition filtering of said organized data;

retrieving data representing end points of said echo-dynamic arc by applying an edge detection algorithm to said organized data;

computing a slope s of a straight line connecting first and second endpoints of said echo-dynamic arc; and computing said angle of refraction $\theta$ as a function of said slope s.

2. The measurement method as defined in claim 1, wherein said organized data is stored in a first-in/first-out buffer.

3. A method for controlling an angle of refraction of a pulsed ultrasonic beam propagating through a solid material after said beam has been transmitted by an ultrasonic transducer to impinge on a surface of said solid material with an initial angle of incidence, comprising the steps of:

acquiring data characterizing an echo-dynamic arc of a B-scan image;

computing a slope s of a straight line connecting first and second endpoints of said echo-dynamic arc; and computing said angle of refraction $\theta$ as a function of said slope s;

computing an angular error equal to a difference between said computed angle of refraction and a desired angle of refraction;

computing a new angle of incidence as a function of said angular error; and adjusting an angle of said transducer so that a transmitted pulsed ultrasonic beam has said new angle of incidence.

4. The control method as defined in claim 3, wherein said data is acquired by the steps of:

transmitting a first pulsed ultrasonic beam and then receiving an echo pulse from a reflector inside said solid material while said transducer is at a first position;

determining a first metal path of said first pulsed ultrasonic beam;

moving said transducer from said first position to a second position;

transmitting a second pulsed ultrasonic beam and receiving an echo pulse from said reflector while said transducer is at said second position; and determining a second metal path of said second pulsed ultrasonic beam, said slope s being computed by computing a ratio of a difference of said first and second metal paths to a distance between said first and second positions.

5. The control method as defined in claim 3, wherein said angle of refraction θ is computed in accordance with a formula:

$$\theta = \arcsin[s].$$

6. The control method as defined in claim 4, further comprising the steps of:

measuring a first round-trip transit time of said first pulsed ultrasonic beam; and measuring a second round-trip transit time of said second pulsed ultrasonic beam, wherein said first and second metal paths are determined as a function of said first and second round-trip transit times, respectively.

7. A method for controlling an angle of refraction of a pulsed ultrasonic beam propagating through a solid material after said beam has been transmitted by an ultrasonic transducer to impinge on a surface of said solid material with an initial angle of incidence, comprising the steps of:

moving said transducer from a first position to a second position;

transmitting a pulsed ultrasonic beam and then receiving an echo pulse from said reflector at each of a plurality of transducer positions along a path from said first position to said second position;

organizing data for the positions of said transducer and data for metal paths corresponding to said position data to represent an echo-dynamic arc;

recognizing said echo-dynamic arc using pattern recognition filtering;

detecting end points of said echo-dynamic arc using an edge detection algorithm;

computing a slope s of a straight line connecting first and second endpoints of said echo-dynamic arc;

computing said angle of refraction θ as a function of said slope s;

computing an angular error equal to a difference between said computed angle of refraction and a desired angle of refraction;

computing a new angle of incidence as a function of said angular error; and adjusting an angle of said transducer so that a transmitted pulsed ultrasonic beam has said new angle of incidence.

8. The control method as defined in claim 3, wherein said new angle of incidence is computed in accordance with Snell's law.

9. The control method as defined in claim 7, wherein said organized data is stored in a first-in/first-out buffer.

10. A system for controlling an angle of refraction of a pulsed ultrasonic beam propagating through a solid material after said beam has been transmitted by an ultrasonic transducer to impinge on a surface of said solid material with an initial angle of incidence, comprising the steps of:

means for moving said transducer from a first position to a second position, said transducer transmitting a pulsed ultrasonic beam and then receiving an echo pulse from said reflector at each of a plurality of transducer positions along a path from said first position to said second position;

means for organizing data for the positions of said transducer and data for metal paths corresponding to said position data to represent an echo-dynamic arc;

means for recognizing said echo-dynamic arc using pattern recognition filtering;

means for detecting end points of said echo-dynamic arc using an edge detection algorithm;

means for computing a slope s of a straight line connecting first and second endpoints of said echo-dynamic arc;

means for computing said angle of refraction θ as a function of said slope s;

means for computing an angular error equal to a difference between said computed angle of refraction and a desired angle of refraction;

means for computing a new angle of incidence as a function of said angular error; and means for adjusting an angle of said transducer so that a transmitted pulsed ultrasonic beam has said new angle of incidence.

11. The system as defined in claim 10 wherein said means for organizing said data comprises a first-in/first-out buffer.

\* \* \* \* \*